United States Patent
Washburn et al.

(10) Patent No.: US 11,827,579 B2
(45) Date of Patent: Nov. 28, 2023

(54) PROCESSES FOR CONVERTING BENZENE AND/OR TOLUENE VIA METHYLATION

(71) Applicant: ExxonMobil Chemical Patents Inc., Baytown, TX (US)

(72) Inventors: Seth M. Washburn, Houston, TX (US); Hsu Chiang, Humble, TX (US); Umar Aslam, Houston, TX (US); Wenyih F. Lai, Bridgewater, NJ (US); Doron Levin, Highland Park, NJ (US); Tan-Jen Chen, Seattle, WA (US)

(73) Assignee: ExxonMobil Technology and Engineering Company, Baytown, TX (US)

(*) Notice: Subject to any disclaimer, the term of this patent is extended or adjusted under 35 U.S.C. 154(b) by 156 days.

(21) Appl. No.: 17/431,745

(22) PCT Filed: Mar. 18, 2020

(86) PCT No.: PCT/US2020/023403
§ 371 (c)(1),
(2) Date: Aug. 18, 2021

(87) PCT Pub. No.: WO2020/197890
PCT Pub. Date: Oct. 1, 2020

(65) Prior Publication Data
US 2022/0119324 A1    Apr. 21, 2022

Related U.S. Application Data

(60) Provisional application No. 62/825,335, filed on Mar. 28, 2019.

(30) Foreign Application Priority Data

Jul. 11, 2019    (EP) .................................. 19185663

(51) Int. Cl.
C07C 2/86    (2006.01)
B01J 29/70    (2006.01)

(52) U.S. Cl.
CPC ............... C07C 2/865 (2013.01); B01J 29/70 (2013.01); B01J 29/7088 (2013.01);
(Continued)

(58) Field of Classification Search
CPC ..... C07C 2/865; C07C 2/864; C07C 2529/70; C07C 2523/00; C07C 2529/06;
(Continued)

(56) References Cited

U.S. PATENT DOCUMENTS

| | | | |
|---|---|---|---|
| 9,440,893 B2 | 9/2016 | Helton et al. | |
| 9,783,462 B2 | 10/2017 | Ghosh et al. | |
| 2004/0097770 A1* | 5/2004 | Dakka | B01J 29/06 585/467 |
| 2008/0103345 A1 | 5/2008 | Levin et al. | |
| 2014/0100402 A1* | 4/2014 | Gawlik | C07C 7/005 585/446 |

(Continued)

FOREIGN PATENT DOCUMENTS

| | | |
|---|---|---|
| CN | 102 372 585 | 3/2012 |
| CN | 105 503 509 | 4/2016 |

(Continued)

*Primary Examiner* — Ali Z Fadhel

(57) ABSTRACT

This disclosure provides improved processes for converting benzene/toluene via methylation with methanol/dimethyl ether for producing, e.g., p-xylene. In an embodiment, a process utilizes a methylation catalyst system comprising a molecular sieve catalyst and an auxiliary catalyst. The auxiliary catalyst comprises a metal element selected from Group 2, Group 3, the lanthanide series, the actinide series, and mixtures and combinations thereof. The auxiliary catalyst may comprise the oxide of the metal element. Deactivation of the molecular sieve catalyst can be reduced with the inclusion of the auxiliary catalyst in the methylation catalyst system.

22 Claims, 3 Drawing Sheets

(52) U.S. Cl.
CPC ........ *C07C 2/864* (2013.01); *B01D 2255/204* (2013.01); *B01D 2255/206* (2013.01); *B01D 2255/2061* (2013.01); *B01D 2255/2063* (2013.01); *B01D 2255/2065* (2013.01); *B01J 2523/20* (2013.01); *B01J 2523/30* (2013.01); *B01J 2523/37* (2013.01); *B01J 2523/3706* (2013.01); *B01J 2523/3712* (2013.01); *C07C 2529/70* (2013.01)

(58) Field of Classification Search
CPC .... B01J 29/70; B01J 29/7088; B01J 2523/20; B01J 2523/30; B01J 2523/37; B01J 2523/3706; B01J 2523/3712; B01D 2255/204; B01D 2255/206; B01D 2255/2061; B01D 2255/2063; B01D 2255/2065; Y02P 20/52
See application file for complete search history.

(56) References Cited

U.S. PATENT DOCUMENTS

| | | |
|---|---|---|
| 2016/0221893 A1 | 8/2016 | Ravishankar et al. |
| 2018/0099913 A1 | 4/2018 | Chen et al. |
| 2018/0170828 A1 | 6/2018 | Schmidt et al. |
| 2018/0170831 A1 | 6/2018 | Jan et al. |
| 2018/0170841 A1 | 6/2018 | Schmidt et al. |
| 2018/0170842 A1 | 6/2018 | Schmidt et al. |
| 2019/0241485 A1 | 8/2019 | Lai et al. |

FOREIGN PATENT DOCUMENTS

| | | |
|---|---|---|
| CN | 107 398 294 | 11/2017 |
| CN | 107 413 375 | 12/2017 |
| CN | 109 603 903 | 4/2019 |
| CN | 109 824 468 | 5/2019 |
| WO | WO99/38823 | 8/1999 |

* cited by examiner

PROCESSES FOR CONVERTING BENZENE AND/OR TOLUENE VIA METHYLATION

CROSS-REFERENCE TO RELATED APPLICATIONS

This application is a US national phase application of PCT Application Serial No. PCT/US2020/023403 having a filing date of Mar. 18, 2020, which claims priority to and the benefit of U.S. Provisional Application No. 62/825,335 having a filing date of Mar. 28, 2019 and European Patent Application No. 19185663.2 having a filing date of Jul. 11, 2019, the disclosures of all of which are incorporated herein by reference in their entireties.

FIELD

This disclosure relates to processes and systems for converting benzene and/or toluene. In particular, this disclosure relates to processes and systems for converting benzene and/or toluene via methylation with methanol and/or dimethyl ether. This disclosure is useful, e.g., in making p-xylene and/or o-xylene via benzene/toluene methylation with methanol.

BACKGROUND 1,4-Dimethylbenzene (para-xylene, or p-xylene) is a valuable chemical feedstock and is used mainly for the production of terephthalic acid and polyethylene terephthalate resins, in order to provide synthetic textiles, bottles, and plastic materials among other industrial applications. As commercial applications of p-xylene have increased, there has been an increased need for more selective processes and increased yields for p-xylene production. Worldwide production capacity of p-xylene is about 40 million tons per year, and the continually increasing demand for purified terephthalic acid in polyester production processes is projected to provide a corresponding demand to the p-xylene market. Thus, there has been a corresponding increase in demand for the development of efficient and cost-effective p-xylene formation and isolation processes.

p-Xylene can be extracted from the BTX aromatics (benzene, toluene and xylene isomers) in the catalytic reformate produced by catalytic reforming of petroleum naphtha. Alternatively, p-xylene can be produced via toluene disproportionation, toluene transalkylation with C9+ aromatics, or toluene methylation with methanol. Regardless of the method of production, p-xylene is then separated out in a series of distillation, adsorption, crystallization and reaction processes from other C8 aromatic isomers, such as meta-xylene, ortho-xylene, and ethylbenzene. The melting point of p-xylene is the highest among such series of isomers, but simple crystallization does not allow easy purification due to the formation of eutectic mixtures. Consequently, current technologies for p-xylene production are energy intensive, and p-xylene separation and purification are a major cost factor in the production of p-xylene. Hence, alternative methods to selectively produce p-xylene are still needed.

The methylation of toluene and/or benzene is a favored route to the formation of p-xylene because of the low cost of starting materials and the potential to provide high yields. One methylation method uses methanol as a methylating agent. Most of the work related to methylation with methanol has concentrated on using selectivated zeolite catalysts, such as steamed phosphorous-containing ZSM-5 (U.S. Pat. Nos. 9,440,893B2 and 9,783,462B2), to increase the p-xylene selectivity in the methylation reaction. A result of using such shape selective catalysts is the need to operate at fairly high temperatures (approx. 500-600° C. or higher), which, in turn, causes rapid catalyst deactivation, significant light gas generation through methanol to olefin chemistry, and production of other trace by-products that have to be removed from the product. In the high temperature process using such selectivated catalysts, essentially all of the methanol can be consumed.

With the growing need for p-xylene there is greater demand for cost effective and efficient synthesis and isolation of p-xylene. One way to increase efficiency and decrease cost would be to suppress catalyst deactivation. The catalyst deactivation rate can affect not only the type of reactor deployed but the cycle time of the catalyst. A challenge that p-xylene manufacturers face is the high cost of catalyst regeneration and, to surmount that challenge, progress toward slowing or stopping catalyst deactivation is needed. Thus, there is a need to slow catalyst deactivation rates which in turn lowers the frequency of catalyst regeneration, and improves upon the production of xylenes.

1,2-Dimethylbenzene (ortho-xylene, or o-xylene) is another valuable chemical intermediate, with demand over the past two decades growing at about 2% per year. o-Xylene is used mainly for the production of phthalic anhydride, a common intermediate in production of plasticizers, dyes, and enteric coatings for pharmaceuticals. As commercial applications of o-xylene continue to increase, there is an increased need for more selective processes and increased yields for o-xylene production. The methylation of toluene can also produce o-xylene.

This disclosure satisfies these and other needs.

References for citing in an Information Disclosure Statement ((37 C.F.R. 1.97(h)): U.S. Pub. Nos. 2018/0099913, 2018/0170828, 2018/0170831, 2018/0170841, 2018/0170842, and 2008/0103345.

SUMMARY

It has been found, in a surprising manner, that by combining an auxiliary catalyst comprising an oxide or an elemental metal of a Group 2, Group 3, the lanthanide series, the actinide series, and mixtures and combinations thereof, with a molecular sieve, e.g., a zeolite of the MWW framework type, one can achieve a significantly reduced catalyst deactivation rate of the molecular sieve in a toluene/benzene-methanol/DME methylation process.

Thus, in a first aspect, this disclosure relates to a process for converting benzene and/or toluene, the process comprising: (a) feeding an aromatic hydrocarbon feed and a methylating agent feed into a methylation reactor, wherein the aromatic hydrocarbon feed comprises benzene and/or toluene, and the methylating agent comprises methanol and/or dimethyl ether; and (b) contacting the aromatic hydrocarbon feed with the methylating agent feed in the presence of a methylation catalyst system in the methylation reactor under methylation conditions effective to produce a methylation product mixture effluent, wherein the methylation catalyst system comprises a molecular sieve catalyst and an auxiliary catalyst, the molecular sieve catalyst comprises a molecular sieve, the auxiliary catalyst comprises a metal element selected from Group 2, Group 3, the lanthanide series, the actinide series, and mixtures and combinations thereof, and the methylation product mixture effluent comprises p-xylene.

In a second aspect, this disclosure provides a process for converting benzene and/or toluene to xylenes, the process comprising: (a) feeding an aromatic hydrocarbon feed and a methylating agent feed into a methylation reactor, wherein the aromatic hydrocarbon feed comprises benzene and/or toluene, and the methylating agent comprises methanol and/or dimethyl ether; and (b) contacting the aromatic hydrocarbon feed with the methylating agent in the presence of a methylation catalyst system under methylation reaction conditions effective to produce a methylation product mixture effluent, wherein the methylation catalyst system comprises a molecular sieve catalyst and an auxiliary catalyst, the molecular sieve catalyst comprises a MWW framework type zeolite, the auxiliary catalyst comprises an oxide of a metal element selected from Group 2, Group 3, the lanthanide series, the actinide series, and mixtures and combinations thereof, and the methylation product mixture effluent comprises p-xylene, the methylation reaction conditions comprise an aromatic inlet feed temperature in a range from 200 to 500° C., an absolute pressure in a range from 100 to 8,500 kPa, a WHSV in a range from 5.0 to 10, and a molar ratio of the aromatic hydrocarbon feed to the methylating agent feed of R(a/m), where $$R(a/m) = \frac{M(tol) + 2 \cdot M(bz)}{M(\text{methanol}) + 2 \cdot M(DME)},$$

M(tol) and M(bz) are the moles of toluene and benzene in the aromatic hydrocarbon feed, respectively, and M(methanol) and M(DME) are the moles of methanol and dimethyl ether in the methylating agent feed, respectively, and 1≤R (a/m)≤5.

DETAILED DESCRIPTION

Figure 1:
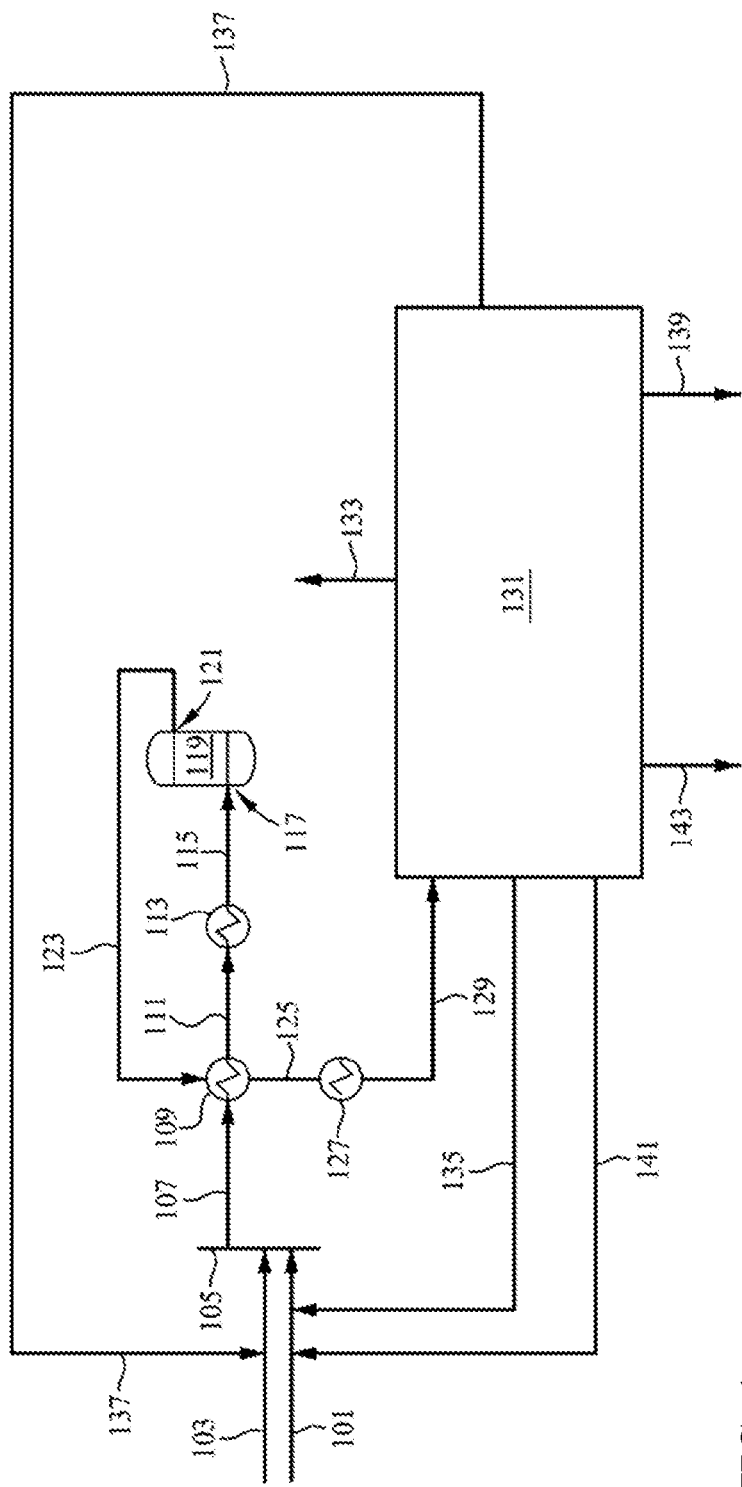
FIG. 1 is a schematic diagram illustrating a process for converting toluene/benzene via methylation with methanol to produce p-xylene, according to an embodiment of this disclosure.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments producing "a xylene" include embodiments where one, two or more xylenes are produced, unless specified to the contrary or the context clearly indicates that only one xylene is produced.

For the purposes of this disclosure, the nomenclature of elements is pursuant to the version of Periodic Table of Elements as described in CHEMICAL AND ENGINEERING NEWS, 63(5), pg. 27 (1985).

The following abbreviations may be used herein for the sake of brevity: RT is room temperature (and is 23° C. unless otherwise indicated), kPag is kilopascal gauge, psig is pound-force per square inch gauge, psia is pounds per square inch absolute, and WHSV is weight hourly space velocity. Abbreviations for atoms are as given in the periodic table (Al=aluminum, for example).

The term "conversion" refers to the degree to which a given reactant in a particular reaction (e.g., methylation, isomerization, etc.) is converted to products. Thus 100% conversion of toluene to xylene in a methylation refers to complete consumption of the toluene, and 0% conversion of the toluene refers to no measurable reaction of the toluene.

The term "selectivity" refers to the degree to which a particular reaction forms a specific product, rather than another product. For example, for the methylation of toluene, 50% selectivity for p-xylene means that 50% of the products formed are p-xylene, and 100% selectivity for p-xylene means that 100% of the product formed is p-xylene. The selectivity is based on the product formed, regardless of the conversion of the particular reaction. The selectivity for a given product produced from a given reactant can be defined as weight percent (wt %) of that product relative to the total weight of the products formed from the given reactant in the reaction.

"Alkylation" means a chemical reaction in which an alkyl group is transferred to an aromatic ring as a substitute group thereon from an alkyl group source compound. "Methylation" means alkylation in which the transferred alkyl group is a methyl. Thus, methylation of benzene can produce toluene, xylenes, trimethylbenzenes, and the like; and methylation of toluene can produce xylenes, trimethylbenzenes, and the like. Toluene methylation with methanol in the presence of a zeolite catalyst can be schematically illustrated as follows:

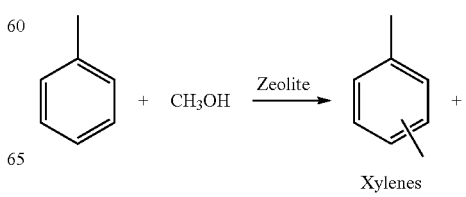

Xylenes

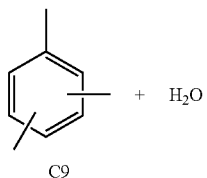 + H₂O

C9

The xylenes include 1,2-dimethylbenzene (ortho-xylene, or o-xylene), 1,3-dimethylbenzene (meta-xylene, or m-xylene), and 1,4-dimethylbenzene (para-xylene, or p-xylene). One or more of these xylene isomers, particularly p-xylene and/or o-xylene, are high-value industrial chemicals. They can be separated to make corresponding products. The C9 hydrocarbons, though, are generally undesirable byproducts. The methylation reaction above can be performed in the presence of a molecular sieve catalyst, such as a zeolite.

As used herein, the term "molecular sieve" means a substance having pores of molecular dimensions that only permit the passage of molecules below a certain size. Examples of molecular sieves include but are not limited to zeolites, silicoaluminophosphate molecular sieves, and the like.

In this disclosure, unless specified otherwise or the context clearly indicates otherwise, "space hourly weight velocity" is based on the combined flow rate of the aromatic hydrocarbon feed and the methylating agent feed and the weight of the molecular sieve catalyst excluding the weight of the auxiliary catalyst.

This disclosure fulfils the need of an effective and efficient process for making p-xylene by toluene/benzene methylation with methanol, in which the catalyst exhibits an exceedingly low deactivation rate. The methylation process utilizes a methylation catalyst system comprising a molecular sieve catalyst and an auxiliary catalyst. The auxiliary catalyst comprises a metal element selected from group 2, group 3, the lanthanides, the actinides, and mixtures and combinations thereof. The metal element may be present in the auxiliary catalyst as an oxide thereof. The presence of the auxiliary catalyst significantly reduces the deactivation rate of the molecular sieve catalyst under the methylation conditions, particularly at a relatively low temperature. Without intending to be bound by a particular theory, it is believed that the presence of the auxiliary catalyst reduces coke formation on the molecular sieve catalyst by scavenging a formaldehyde intermediate formed in the process, which can lead to coke formation if not mitigated.

Toluene alkylation with methanol can be accomplished using MWW framework type molecular sieve catalysts at lower temperatures. The use of the MWW molecular sieve catalysts at lower temperature generates no to very little light gas or many of the other by-products. This has significant capital savings as separation and purification of the light gas, as well as other unwanted by-products generated at high temperature, is no longer needed. Furthermore, costs related to catalyst regeneration and energy consumption are decreased at the lower temperature thereby decreasing operation costs.

The selectivity to xylenes in the process can be on the order of 80%, with the main by-products being benzene and C9+ aromatics. The benzene and/or toluene can be separated from the methylation product mixture effluent and recycled back to the methylation reactor(s), while the C9+ aromatics can be separated for blending into the gasoline pool or transalkylated with additional benzene and/or toluene to make additional xylenes. The life of the molecular sieve catalyst is enhanced as compared with existing processes because the addition of a metal oxide auxiliary catalyst lowers deactivation rates. Moreover, the use of an auxiliary catalyst provides further advantages to a lower temperature benzene and/or toluene conversion process using large pore molecular sieves as the catalyst, advantages may include one or more of: (i) greater diffusion limits that allow the alkylation to be carried out at commercially viable weight hourly space velocities (WHSVs), (ii) lower methanol degradation at lower temperatures, (iii) substantially no light gas production which allows easier and less costly purification, (iv) high selectivity to the para-isomer, and (v) higher weight hourly space velocities (WHSVs) than allowed with smaller pore molecular sieves.

Process for Converting Benzene and/or Toluene Via Methylation

The feeds to the present process include an aromatic hydrocarbon feed, comprising benzene and/or toluene, and a methylating agent feed comprising methanol and/or dimethyl ether. Any suitable refinery aromatic feed can be used as the source of the benzene and/or toluene. In some embodiments, the aromatic hydrocarbon feed comprises toluene at a concentration ≥90 wt % (e.g., ≥92 wt %, ≥94 wt %, ≥95 wt %, ≥96 wt %, ≥98 wt %, or even ≥99 wt %), based on the total weight of the aromatic hydrocarbon feed. In some embodiments, the aromatic hydrocarbon feed may be pre-treated to remove catalyst poisons, such as nitrogen and sulfur-compounds. The aromatic hydrocarbon feed may be fed as a single or multiple streams with the same or different compositions into the methylation reactor via one or more feed inlets. The methylating agent feed may be fed as a single or multiple streams with the same or different compositions into the methylation reactor via one or more feed inlets. Alternatively or additionally, at least a portion of the aromatic feed and at least a portion of the methylating agent feed may be combined and then fed into the methylation reactor as a single or multiple stream via one or more inlets.

The methylation process of this disclosure can be advantageously conducted at relatively low methylation reactor (methylation vessel) temperatures, for example ≤500° C., such as ≤475° C., ≤450° C., ≤425° C., or ≤400° C. A process may be conducted at temperatures of ≥200° C., such as ≥250° C., or ≥300° C. in the methylation reactor which has been found to provide commercially viable methylation reaction rates, for example methylation processes performed at a weight hourly space velocity of the combined feeds from 1 hour$^{-1}$ to 50 hour$^{-1}$. The process may be conducted at temperatures from 200° C. to 500° C., such as from 300° C. to 475° C., from 275° C. to 450° C., or from 250° C. to 400° C. Such low-temperature reaction can be particularly utilized when a MWW framework type zeolite is present in the molecular sieve catalyst. Such low-temperature reaction can be particularly advantageous where a fixed bed of the methylation catalyst system is present in the methylation reactor. The ability of the processes of this disclosure to be operated at low temperature carries many advantages, to name a few: higher energy efficiency, longer catalyst life, fewer species of byproducts, and small quantities of byproducts that otherwise would be produced at higher temperatures, compared to conventional benzene/toluene methylation processes operated at temperatures higher than 500° C.

Operating pressures in the methylation reactor can vary with temperature but in some embodiments are ≥100 kPa, such as ≥1000 kPa, ≥1500 kPa, ≥2000 kPa, ≥3000 kPa, or ≥3500 kPa, to ≤8500 kPa, such as ≤7000 kPa, or ≤6000 kPa. For example, operating pressures may range from 700 kPa to 7000 kPa, such as from 1000 kPa to 6000 kPa, or from 2000 kPa to 5000 kPa. In at least one embodiment, the combination of a high pressure (e.g., a pressure from 1500 kPa to 8500 kPa, such as from 4000 kPa to 6000 kPa) and a low temperature (e.g., a temperature from 250° C. to 500° C.), decreases the amount of light gases produced in the methylation reaction, and may also decrease the catalyst aging rate.

WHSV values based on total aromatic hydrocarbon feed and methylating agent feed and the weight of the molecular sieve catalyst (excluding the weight of the auxiliary catalyst) can range from, e.g., 0.5 hour$^{-1}$ to 50 hour$^{-1}$, such as from 5 hour$^{-1}$ to 15 hour$^{-1}$, from 1 hour$^{-1}$ to 10 hour$^{-1}$, from 5 hour$^{-1}$ to 10 hour$^{-1}$, or from 6.7 hour$^{-1}$ to 10 hour$^{-1}$. In some embodiments, at least part of the aromatic hydrocarbon feed, the methylating agent feed and/or the methylation product mixture effluent may be present in the methylation reactor in the liquid phase. As is described in more detail below, alteration of the WHSV may be desired as reaction temperature changes in order to maintain desired conversion of benzene, toluene, methanol, and/or dimethyl ether.

The methylation reaction can be conducted in a methylation reactor, which can be any suitable reactor system including, but not limited to, a fixed bed reactor, a moving bed reactor, a fluidized bed reactor, and/or a reactive distillation unit. In addition, the methylation reactor may include a single methylation zone or multiple methylation zones located in the same or different reactors. A methylation reactor may include a bed of catalyst particles disposed therein where the particles have insignificant motion in relation to the bed (a fixed bed). In addition, injection of the methylating agent feed can be effected at a single point in the methylation reactor or at multiple points spaced along the methylation reactor. The aromatic hydrocarbon feed and the methylating agent feed may be premixed before entering the methylation reactor.

In certain embodiments of the invention, the methylation reactor includes a single fixed bed or a plurality of fixed beds, continuous flow-type reactors in a down flow mode, where the reactors may be arranged in series or parallel. The methylation reactor may include a single or multiple catalyst beds in series and/or in parallel. The catalyst beds may have various configurations such as: a single bed, several horizontal beds, several parallel packed tubes, multiple beds each in its own reactor shell, or multiple beds within a single reactor shell. In certain embodiments, the fixed beds provide uniform flow distribution over the entire width and length of the bed to utilize substantially all of the methylation catalyst system. In at least one embodiment, the methylation reactor can provide heat transfer from a fixed bed to provide effective methods for controlling temperature.

The concentration of methylating agent feed can be adjusted by, e.g., staged additions thereof. By staged additions, aromatic hydrocarbon/methylating agent feed concentrations can be maintained at optimum levels for desirable benzene and/or toluene conversion. In at least one embodiment, the ratio of aromatic hydrocarbon feed to methylating agent feed is R(a/m) which is determined by the following equation:

$$R(a/m) = \frac{M(tol) + 2 \cdot M(bz)}{M(\text{methanol}) + 2 \cdot M(DME)}$$

Where M(tol) is the moles of toluene in the aromatic hydrocarbon feed, M(bz) is the moles of benzene in the aromatic hydrocarbon feed, M(methanol) is the moles of methanol in the methylating agent feed, and M(DME) is the moles of dimethyl ether in the methylating agent feed. In various embodiments, R(a/m) is ≥1, ≥2, or ≥2.5, and ≤6, ≤5, or ≤4, or ranges from 1 to 5 or from 2 to 4. For the purpose of producing xylenes, each benzene molecule needs to be methylated by two methanol molecules or one DME molecule, and each toluene by one methanol molecule or half a DME molecule. Over-methylation of benzene and/or toluene can result in the production undesirable C9+ aromatic hydrocarbons as byproducts. To prevent over-methylation, it is highly desirable that R(a/m)≥1.5. Preferably 2≤R(a/m)≤5. More preferably 2≤R(a/m)≤4. The efficiency of the methylation process can be reduced at higher R(a/m), e.g., R(a/m)>5, due to large quantity of toluene/benzene present in the methylation reaction product mixture effluent, which needs to be separated and recycled to the methylation reactor.

The efficiency of a methylation reactor containing a fixed bed of methylation catalyst system may be affected by the pressure drop across the fixed bed. The pressure drop depends on various factors such as the path length, the catalyst particle size, and pore size. A pressure drop that is too large may cause channeling through the catalyst bed, and poor efficiency. In some embodiments, the methylation reactor has a cylindrical geometry with axial flows through the catalyst bed.

The various designs of the methylation reactor may accommodate control of specific process conditions, e.g. pressure, temperature, and WHSV. The WHSV determines volume and residence time that may provide the desired conversion.

The product of the methylation reaction, the methylation product mixture effluent, can comprise: xylenes, benzene, and/or toluene (both residual and coproduced in the process), C9+ aromatic hydrocarbons, co-produced water, and unreacted methanol and DME. In some embodiments, the process is operated at sufficient WHSV so that only a portion of the methanol is reacted with the aromatic hydrocarbon feed and the methylation product mixture effluent contains residual methanol and/or DME.

The temperature of the methylation zone will affect by-product formation and a temperature lower than 500° C. may decrease light gas formation. In some embodiments, the methylation product mixture effluent contains ≤10 wt %, such as ≤5 wt %, ≤2 wt %, ≤1 wt %, or is substantially free of light gases generated by methanol decomposition to ethylene or other olefins.

In some embodiments, the methylation product mixture effluent is separated into an aqueous phase and an oil phase. The method of separating the aqueous phase from the oil phase can be accomplished by a coalescing plate separator, e.g., described in U.S. Pat. Nos. 4,722,800 and 5,068,035; a centrifugal separator, e.g., described in U.S. Pat. Nos. 4,175,040; 4,959,158; and 5,591,340; a hydrocyclone separator, e.g., described in U.S. Pat. Nos. 4,428,839; 4,927,536; and 5,667,686; or other suitable methods. In some embodiments, the oil phase of the methylation product mixture effluent may contain at least 80 wt % xylenes. In some embodiments, the methylation product mixture effluent comprising an aqueous phase and an oil phase enters a first separation unit; the aqueous phase, which is denser, settles to the bottom of an upstream chamber and can be drawn from the water drain tube down below. The oil phase, which is lighter, is located on top of the aqueous phase and can spill over a dividing wall to the downstream chamber where it can then be drawn from the bottom of the downstream chamber.

After separation of the aqueous phase, the oil phase may be separated into a DME-rich stream, an aromatics-rich stream, and methane or other by-products. In some embodiments, the DME-rich stream may be fully or partially separated from other products and by-products to be recycled through a first recycling channel. In some embodiments, the DME-rich stream contains DME in ≥50 wt %, ≥60 wt %, ≥70 wt %, ≥80 wt %, ≥90 wt %, ≥95 wt %, ≥98 wt %, or ≥99 wt %, based on the total weight of the DME-rich stream. In some embodiments, the methylating agent feed contains DME from the is DME-rich stream in ≥20 wt %, ≥40 wt %, ≥60 wt %, ≥80 wt %, ≥90 wt %, ≥95 wt %, ≥98 wt %, or ≥99 wt %, based on the total weight of the DME in the methylating agent stream. In at least one embodiment all of the DME in the methylation agent feed is obtained from the DME-rich stream.

In some embodiments, methane is partially or fully separated from other products, and by-products. In at least one embodiment, the methane is used as fuel gas.

In some embodiments, the aromatics-rich stream comprises C6 to C9+ aromatic hydrocarbon products and by-products. In another embodiment, the aromatics-rich stream is further separated to produce a C9+ process stream containing C9+ aromatics. In at least one embodiment, the C9+ process stream can be recovered for blending into the gasoline pool or transalkylated with benzene and/or toluene to make additional xylenes. In some embodiments, the aromatics-rich stream comprises xylenes in ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream. In some embodiments, the aromatics-rich stream comprises p-xylene. In some embodiments, the aromatics-rich stream contains p-xylene in greater than ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream.

In some embodiments the DME-rich stream and the aromatics-rich stream are separated in a distillation system including one or more distillation columns. The distillation system may be operated at increased pressure, such as greater than ≥400 kPag, ≥500 kPag, ≥600 kPag, ≥700 kPag, ≥800 kPag, ≥900 kPag, such as from 400 kPag to 1400 kPag, from 600 kPag to 1300 kPag, from 700 kPag to 1200 kPag, from 800 kPag to 1100 kPag, or from 900 kPag to 1000 kPag.

In some embodiments, the aromatics-rich stream is further separated into a xylenes-rich stream and a toluene-rich stream, which may comprise benzene. The toluene-rich stream comprising benzene and/or toluene to be recycled through a second recycling channel may contain toluene in ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In another embodiment, the toluene-rich stream comprises benzene and toluene in a combined wt % of ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In some embodiments, the xylenes-rich stream contains an equilibrium mixture of ortho-, meta-, para-xylenes comprising about 24 wt % of p-xylene, about 50 wt % of meta-xylene, and about 26 wt % of ortho-xylene. The xylenes-rich stream may contain p-xylene in ≥10 wt %, ≥20 wt %, ≥30 wt %, ≥40 wt %, ≥50 wt %, ≥60 wt %, ≥70 wt %, or ≥80 wt %, based on the total weight of the xylenes-rich stream.

The xylenes-rich stream may be sent to a separation/recovery system to recover a high-purity p-xylene product and an optional o-xylene product. A xylenes loop can comprise a p-xylene recovery unit, such as a crystallization separation unit and/or an adsorptive chromatography separation unit known in the prior art. The p-xylene recovery unit can produce a high-purity p-xylene product and a p-xylene-deleted stream rich in o-xylene and m-xylene. The xylenes-loop can further comprise an isomerization unit such as a vapor-phase isomerization unit and/or a liquid phase isomerization unit known in the prior art to further convert a portion of the o-xylene and m-xylene in the p-xylene-depleted stream to p-xylene. The isomerized stream can be recycled to the p-xylene recovery unit in the xylenes loop to recover additional quantity of p-xylene.

In certain embodiments, the aqueous phase is separates a methanol-rich stream from a water-rich stream. In some embodiments, the methanol-rich stream contains methanol at ≥50 wt %, ≥60 wt %, ≥70 wt %, ≥80 wt %, ≥90 wt %, ≥95 wt %, ≥98 wt %, or ≥99 wt %, based the overall weight of the methanol-rich stream. In at least one embodiment, the methanol rich stream is recycled to the methylation agent feed or the methylation reactor. In some embodiments, the separation of the methanol-rich stream from the water-rich stream is accomplished by a distillation system; an example system is described in U.S. Pat. Nos. 3,293,154 and 4,210,495.

In another embodiment, the DME-rich stream is combined with the methanol-rich stream to form a single recycle stream. In another embodiment, the toluene-rich stream, the DME-rich stream, and the methanol-rich stream are combined to form a single recycle stream.

The Molecular Sieve Catalyst

Any suitable molecular sieve capable of catalyzing conversion of toluene and/or benzene to xylenes with methanol and/or DME can be used for the methylation processes of this disclosure. Examples of such catalysts are crystalline microporous materials such as zeolite-based, as well as non-zeolite-based, molecular sieves and can be of the large, medium, or small pore type. Molecular sieves can have 3-dimensional, four-connected framework structure of corner-sharing $[TO_4]$ tetrahedra, where T can be a tetrahedrally coordinated atom. These molecular sieves are often described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al, *Introduction to Zeolite Science and Practice*, Second Completely Revised and Expanded Edition, Volume 137, pages 1-67, Elsevier Science, B.V., Amsterdam, Netherlands (2001). Another convenient measure of the extent to which a molecular sieve provides control of molecules of varying sizes to its internal structure is the Constraint Index. The method by which Constraint Index is determined is described fully in U.S. Pat. No. 4,016,218, which is incorporated herein by reference for details of the method.

Non-limiting examples of molecular sieves include small pore molecular sieves (e.g., AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof), medium pore molecular sieves (e.g., AFO, AEL, EUO, HEU, FER, MEL, MFI, MTW, MTT, TON, and substituted forms thereof), large pore molecular sieves (e.g., EMT, FAU, and substituted forms thereof), intergrowths thereof, and combinations thereof. Other molecular sieves include, but are not limited to, ANA, BEA, CFI, CLO, DON, GIS, LTL, MER, MOR, MWW, SOD, intergrowths thereof, and combinations thereof. In some embodiments, the molecular sieve has an MWW framework type (morphology).

The small, medium, and large pore molecular sieves have from a 4-ring to a 12-ring or greater framework-type. In some embodiments, the zeolitic molecular sieves have 6-, 8-, 10-, or 12-ring structures and an average pore size in the range from about 3 Å to 15 Å. In other embodiments, the molecular sieves are aluminosilicate molecular sieves and have a 6-ring or an 8-ring structure and an average pore size of about 5 Å or less, such as in the range from 3 Å to about 5 Å, for example from 3 Å to about 4.5 Å or from 3.5 Å to about 4.2 Å.

Other non-limiting examples of zeolitic and non-zeolitic molecular sieves include one or a combination of the following: Beta (U.S. Pat. No. 3,308,069 and Reissue No. 28,341), ZSM-3 (U.S. Pat. No. 3,415,736), ZSM-4 (U.S. Pat. No. 4,021,947), ZSM-5 (U.S. Pat. Nos. 3,702,886, 4,797,267 and 5,783,321), ZSM-11 (U.S. Pat. No. 3,709, 979), ZSM-12 (U.S. Pat. No. 3,832,449), ZSM-12 and ZSM-38 (U.S. Pat. No. 3,948,758), ZSM-14 (U.S. Pat. No. 3,923,636), ZSM-18 (U.S. Pat. No. 3,950,496), ZSM-20 (U.S. Pat. No. 3,972,983), ZSM-22 (U.S. Pat. No. 5,336, 478), ZSM-23 (U.S. Pat. No. 4,076,842), ZSM-34 (U.S. Pat. No. 4,086,186), ZSM-35 (U.S. Pat. No. 4,016,245), ZSM-38, ZSM-48 (U.S. Pat. No. 4,397,827), ZSM-50, ZSM-58 (U.S. Pat. No. 4,698,217), MCM-1 (U.S. Pat. No. 4,639, 358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880, 611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362, 697), ALPO-11 (U.S. Pat. No. 4,310,440), ultrastable Y zeolite (USY) (U.S. Pat. Nos. 3,293,192 and 3,449,070), Dealuminized Y zeolite (Deal Y) (U.S. Pat. No. 3,442,795), mordenite (naturally occurring and synthetic) (for synthetic mordenite U.S. Pat. Nos. 3,766,093 and 3,894,104), SSZ-13, titanium aluminosilicates (TASOs) such as TASO-45 (European Patent No. EP-A-0 229 295), boron silicates (U.S. Pat. No. 4,254,297), titanium aluminophosphates (TAPOs) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), those disclosed in International Publication No. WO 98/57743 published Dec. 23, 1988 (molecular sieve and Fischer-Tropsch), those disclosed in U.S. Pat. No. 6,300,535 (MFI-bound zeolites), mesoporous molecular sieves (U.S. Pat. Nos. 6,284,696, 5,098,684, 5,102,643 and 5,108,725), and the like, and intergrowths and/or combinations thereof.

In an embodiment, the methylation catalyst comprises an aluminosilicate methylation catalyst system. Aluminosilicates, as used herein, can include those having a molar relationship of $X_2O_3$:(n)$YO_2$ (wherein X is a trivalent element e.g. Al and Y is a tetravalent element e.g. Si), in which n≤500, such as ≤250, ≤100, such as from 30 to 100.

Non-limiting examples of trivalent X can include aluminum, boron, iron, indium, gallium, and combinations thereof. Non-limiting examples of tetravalent Y can include silicon, tin, titanium, germanium, and combinations thereof.

In embodiments where X represents aluminum and Y represents silicon, the factor n represents a silica:alumina ratio, also termed Si:$Al_2$. Another measure of relative proportion in such cases is the ratio of Y:X, or the silicon:aluminum ratio. In one embodiment, the silicon:aluminum (Si:Al) ratio of aluminosilicates is ≤500, such as ≤250, ≤100, or ≤50, such as from 1 to 50, from 5 to 50, or from 15 to 50.

Other non-limiting examples of aluminosilicate catalysts and compositions can be found, for instance, in U.S. Patent Application Publication No. 2003/0176751 and U.S. patent application Ser. No. 11/017,286 (filed Dec. 20, 2004) and 60/731,846 (filed Oct. 31, 2005).

One class of molecular sieve suitable for use in a process of this disclosure has a Constraint Index ≤5, and is crystalline microporous material of the MWW framework type. MWW framework type refers to a type of crystalline microporous material that comprises at least two independent sets of 10-membered ring channels and has composite building units of d6r (t-hpr) and mel as defined and discussed in *Compendium of Zeolite Framework Types. Building Schemes and Type Characteristics* Van Koningsveld, Henk, (Elsevier, Amsterdam, 2007), incorporated by reference. Crystalline microporous materials of the MWW framework type can include those molecular sieves having an X-ray diffraction pattern comprising d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system. Crystalline microporous materials of the MWW framework type include molecular sieves having natural tiling units of t-dac-1, t-euo, t-hpr, t-kah, t-kzd, t-mel, t-mww-1, t-mww-2, and t-srs as defined and discussed in *Three periodic Nets and Tilings: Natural Tilings for Nets*, V. A. Blatov, O. Delgado-Friedrichs, M. O'Keeffe and D. M. Proserpio, Acta Crystallogr. A 63, 418-425 (2007), incorporated by reference.

In at least one embodiment, the crystalline microporous material is a zeolite. As used herein, the term "crystalline microporous material of the MWW framework type" comprises one or more of:

(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, incorporated herein by reference);

(b) molecular sieves made from a second degree building block, being a 2-dimensional tiling of such MWW framework topology unit cells, forming a monolayer of one unit cell thickness, in one embodiment, one c-unit cell thickness;

(c) molecular sieves made from common second degree building blocks, being layers of one or more than one unit cell thickness, where the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and (d) molecular sieves made by any regular or random 2-dimensional or 3-dimensional combination of unit cells having the MWW framework topology.

Examples of crystalline microporous materials of the MWW framework type include MCM-22 (U.S. Pat. No. 4,954,325), PSH-3 (U.S. Pat. No. 4,439,409), SSZ-25 (U.S. Pat. No. 4,826,667), ERB-1 (European Patent No. 0293032), ITQ-1 (U.S. Pat. No. 6,077,498), ITQ-2 (International Publication No. WO97/17290), MCM-36 (U.S. Pat. No. 5,250, 277), MCM-49 (U.S. Pat. No. 5,236,575), MCM-56 (U.S. Pat. No. 5,362,697), UZM-8 (U.S. Pat. No. 6,756,030), UZM-8HS (U.S. Pat. No. 7,713,513), UZM-37 (U.S. Pat. No. 7,982,084), EMM-10 (U.S. Pat. No. 7,842,277), EMM-12 (U.S. Pat. No. 8,704,025), EMM-13 (U.S. Pat. No. 8,704,023), UCB-3 (U.S. Pat. No. 9,790,143B2), and mixtures thereof.

In some embodiments, the crystalline microporous material of the MWW framework type may be contaminated with other crystalline materials, such as ferrierite or quartz. These contaminants may be present in quantities of ≤10 wt %, such as ≤5 wt %.

In some embodiments, the molecular sieves are not subjected to pre-treatments, such as high temperature steaming, to modify their diffusion properties. In other embodiments, the molecular sieves may be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350° C. to 550° C. A suitable silica-selectivation procedure is described in U.S. Pat. No. 5,476,823. In another embodiment, the catalyst is selectivated by contacting the catalyst with steam. Steaming of the zeolite is effected at a temperature of ≥950° C., such as from 950° C. to 1075° C., or from 1000° C. to 1050° C., for 10 minutes to 10 hours, such as from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026. In some embodiments, a combination of silica selectivation, steam selectivation, and/or coke selectivation may be employed.

It may be desirable to combine the molecular sieve, prior to selectivating, with at least one oxide modifier, such as at least one oxide selected from elements of Groups 2 to 4 and 13 to 16 of the Periodic Table. In at least one embodiment, the oxide modifier is an auxiliary catalyst. In some embodiments, the oxide modifier is selected from oxides of boron, magnesium, calcium, lanthanum, and phosphorus. In some cases, the molecular sieve may be combined with more than one oxide modifier, for example a combination of oxides of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be from 0.05 wt % and 20 wt %, such as from 0.1 wt % to 10 wt %, based on the weight of the final catalyst. Where the modifier comprises phosphorus, incorporation of modifier into the catalyst is conveniently achieved by the methods described in U.S. Pat. Nos. 4,356,338; 5,110,776; 5,231,064; and 5,348,643.

The molecular sieves may be used as the methylation catalyst without any binder or matrix, in a self-bound form. Alternatively, the molecular sieves may be composited with another material which is resistant to the temperatures and other conditions employed in the methylation reaction. Such binder or matrix materials can comprise active and/or inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels comprising mixtures of silica and metal oxides. Clays may also be included with the oxide type binders to modify the mechanical properties of the catalyst or to assist in its manufacture. Use of a material in conjunction with the molecular sieve whether combined therewith or present during its synthesis, which itself is catalytically active may be termed an auxiliary catalyst. Inactive materials suitably serve as diluents to control the amount of conversion so that products may be obtained economically and orderly without employing other means for controlling the rate of reaction. These materials may be incorporated into naturally occurring clays, for example, bentonite and kaolin, to improve the crush strength of the catalyst under commercial operating conditions and function as binders or matrices for the catalyst. The relative proportions of molecular sieve and auxiliary catalyst vary widely, with the sieve content ranging from 1 wt % to 90 wt %, and in some embodiments the composite is prepared in the form of beads, in the range of 2 wt % to 80 wt % of the composite.

Auxiliary Catalyst

Methylation catalysts may undergo deactivation with time and/or use, and it has been discovered that addition of certain auxiliary catalysts may extend the useful life of the methylation catalysts. Without being limited by theory, it is possible that methylation catalysts comprising molecular sieves are deactivated by coke formation and, furthermore, that coke formation may develop from formaldehyde produced by methanol degradation. It is possible that certain auxiliary catalysts function by removal of formaldehyde or decreasing coke formation. Nonetheless, it has been discovered that certain auxiliary catalysts can inhibit catalyst deactivation and improve catalyst lifetime, thereby decreasing the frequency of catalyst regeneration and decreasing the overall cost of the process.

An auxiliary catalyst can be present in many forms and, as follows, in varying degrees of increasing proximity to the methylation catalyst forming a methylation catalyst system. For instance, an auxiliary catalyst comprising an active metal oxide can be present as particulate matter separate from the formulated methylation catalyst system particles. Also, a metal oxide auxiliary catalyst can be present as a component of the formulated methylation catalyst system particles. Additionally, a metal oxide auxiliary catalyst can be coated on the surface and/or in the pores of the methylation catalyst itself. In one embodiment, the methylation catalyst system contains an auxiliary catalyst comprising active metal oxides.

In some embodiments, the methylation catalyst system comprises a physical mixture of the metal oxide and methylation catalyst as opposed to incorporation of the metal into the molecular sieve structure or the internal pore structure of the molecular sieve (e.g. incipient wetness impregnation). The physical mixture may comprise e.g., an extrudate of a mixture of the metal oxide and the methylation catalyst, or a blend of particles of the metal oxide with particles of the methylation catalyst.

Active metal oxides are those metal oxides, different from typical binders and/or matrix materials that, when used as an auxiliary catalyst in combination with a methylation catalyst in a methylation catalyst system, are effective in extending the useful life of the methylation catalyst. Quantification of the extension in catalyst life is determined by the Lifetime Enhancement Index (LEI) which is the ratio of the lifetime of the catalyst with auxiliary catalyst present to the lifetime of the catalyst without auxiliary catalyst present, in the same process under the same conditions. The lifetime of the catalyst is determined by the cumulative amount of feedstock processed per gram of methylation catalyst until the conversion of feedstock by the methylation catalyst system falls below some defined level, for example 10%. An inactive metal oxide will have little to no effect on the lifetime of the methylation catalyst, or will shorten the lifetime of the methylation catalyst, and will therefore have an LEI less than or equal to 1. Thus, active metal oxides are those metal oxides, and when used in combination with a methylation catalyst, provide a methylation catalyst system that has an LEI greater than 1. By definition, a methylation catalyst that has not been combined with an active metal oxide will have an LEI equal to 1.0.

It has been found that, a catalyst system comprising an auxiliary catalyst, wherein the auxiliary catalyst comprises metal oxides, in combination with a methylation catalyst, a methylation catalyst system can be produced having an LEI from greater than 1 to 200, for example from 1.5 to 100. Methylation catalyst systems can exhibit LEI values greater than 1.1, greater than 1.2, greater than 1.3, greater than 1.5, greater than 1.7, or greater than 2, for example from 1.1 to 25, from 1.2 to 20, or from 1.5 to 15. In at least one embodiment, the active metal oxide when combined with a methylation catalyst comprising a molecular sieve in a methylation catalyst system enhances the lifetime of the methylation catalyst in the conversion of an aromatic hydrocarbon feed comprising benzene or toluene into one or more xylenes.

Non-limiting examples of basic metal oxides include, but are not limited to, hydrotalcite, oxides of metals in Group 2 of the Periodic Table of Elements, oxides of metals in Group 3 of the Periodic Table of Elements, a mixed metal oxide containing one or more metals of Groups 2 and 3 of the Periodic Table of Elements, or combinations thereof. As used herein, Group 3 metals from the Periodic Table of Elements should be understood to include lanthanide series metals and actinide series metals. In one embodiment, an auxiliary catalyst comprises an oxide of yttrium. The metal oxide may itself be supported on a porous inorganic support material, preferably one which is basic or neutral in character so as not to impose any undesired competing reactions. A function of the support is to improve the dispersion of the active metal oxide(s) so a greater number of active sites are available for intercepting formaldehyde and to this end, high dispersion and high surface area are desirable attributes. Suitable porous metal oxide supports include zirconia ($ZrO_2$), titania ($TiO_2$), silica ($SiO_2$), ceria ($CeO_2$), magnesia (MgO), monohydrocalcite, non-acidic aluminas or mixture(s) thereof. A suitable amount of support relative to the active basic metal oxide is ≤50 wt %, e.g. 5, 10, 20 or 25 wt %. The amount of support can be selected according to the surface area and porosity of the support and its ability to disperse the active oxide in proximity to the sieve. For example, a suitable supported active metal oxide is 5-10 wt % $La_2O_3/ZrO_2$.

In one embodiment, in which an auxiliary catalyst is present in combination with the methylation catalyst, the weight/weight ratio of methylation catalyst (alone, without binder, matrix, etc.) to metal oxide auxiliary catalyst can be from 100:1 to 1:2, such as from 50:1 to 1:1, 25:1 to 3:2 or 10:1 to 2:1. For example, the weight percentage of auxiliary catalyst based on the combined weight of the methylation catalyst and the auxiliary catalyst may be from 1 wt % to 66 wt %, such as from 1 wt % to 50 wt %, from 2 wt % to 50 wt %, from 4 wt % to 40 wt %, from 5 wt % to 30 wt %, or from 10 wt % to 30 wt %.

Metal oxide(s) can be prepared using a variety of methods. For example, a metal oxide can be made from a metal oxide precursor, such as a metal salt, such as a metal halide, nitrate, sulfate, or acetate. Other suitable sources of metal oxides include compounds that form metal oxides during calcination, such as oxychlorides and nitrates. In one embodiment, the metal oxide is made from a hydrated metal oxide precursor. Hydrated metal oxide precursors, such as hydrated yttria, are disclosed, for example, in U.S. Pat. No. 5,728,644, incorporated by reference. According to one method, the active metal oxide is prepared by the thermal decomposition of metal-containing compounds, such as scandium oxalate, at high temperatures, such as 650° C., in flowing air, as described in U.S. Pat. No. 4,980,141, incorporated by reference. In another method, the active metal oxide is prepared by the hydrolysis of metal-containing compounds followed by dehydration and calcination. In yet another method, the active metal oxide is prepared by the aerogel method (Koper, O. B., Lagadic, I., Volodin, A. and Klabunde, K. J. Chem. Mater. 1997, 9, 2468-2480). Other aspects of metal oxides and their preparation can be found, e.g., in U.S. Patent Application Publication No. 2003/0171633 A1 and U.S. Pat. No. 6,995,111, each incorporated by reference.

In one embodiment where hydrated metal oxide precursors are utilized, the hydrated metal oxide precursor can be hydrothermally treated under conditions that include a temperature of about 80° C. or more, such as about 100° C. or more. The hydrothermal treatment may take place in a sealed vessel at greater than atmospheric pressure. Alternatively, the hydrothermal treatment is performed using an open vessel under reflux conditions. Agitation of hydrated metal oxides in a liquid medium, for example, by the action of refluxing liquid and/or stirring, can promote the effective interaction of the hydrated oxide with the liquid medium. The duration of the contact of the hydrated oxide with the liquid medium can be about 1 hour or longer, about 2 hours or longer, about 4 hours or longer, or about 8 hours or longer, such as from about 1 hour to about 4 hours, from about 2 hours to about 6 hours, or about 4 hours to about 10 hours. The liquid medium for this treatment may have a pH of about 6 or greater, such as about 8 or greater. Non-limiting examples of suitable liquid media include water, hydroxide solutions (such as hydroxides of $NH_4^+$, $Na^+$, $K^+$, $Mg^{2+}$, and $Ca^{2+}$), carbonate and bicarbonate solutions (such as carbonates and bicarbonates of $NH_4^+$, $Na^+$, $K^+$, $Mg^{2+}$, and $Ca^{2+}$), pyridine and its derivatives, and alkyl/hydroxyl amines.

In another embodiment, a metal oxide is prepared, for example, by subjecting a liquid solution, such as an aqueous solution, comprising a source of ions of a desired metal to conditions sufficient to cause precipitation of a hydrated precursor of the solid oxide material, such as by the addition of a precipitating reagent to the solution. Conveniently, the precipitation can be conducted at a pH above 7. For example, the precipitating agent may be a base, such as sodium hydroxide or ammonium hydroxide.

Various other methods exist for making mixed metal oxide precursors, e.g., wet impregnation, incipient wetness, and co-precipitation, inter alia.

FIG. 1 schematically illustrates a process for converting benzene and/or toluene via methylation with methanol and/or DME to produce p-xylene according to at an embodiment of this disclosure. Methylating agent feed 101, comprising methanol and/or DME is combined with aromatic hydrocarbon feed 103 comprising toluene and/or benzene in fluid transfer line 105. Fluid transfer line 105 may contain an agitator or other mixing device (not shown) in order to combine methylating agent feed 101 and aromatic hydrocarbon feed 103 to form a combined feed. The combined feed is fed by line 107 to heat exchanger 109 to pre-heat the combined feed. The heated combined feed comprising a mixture of feed 101 and feed 103 is fed through line 111 to heat exchanger 113. Heat exchanger 113 may be used to heat or cool the combined feed as necessary. The combined feed is then passed through line 115, through inlet 117 to methylation reactor 119. Line 115 may also include a pump or series of pumps (not shown) in order to maintain sufficient pressure and WHSV in methylation reactor 119. Inlet 117 may accept one or more feeds or streams comprising one or more recycle channels. Methylation reactor 119 can be a fixed or fluid bed reactor containing the methylation catalyst (not shown) and auxiliary catalyst (not shown) and is operated at methylation reaction conditions, which may include temperatures less than 500° C. and pressures greater than 100 kPa. Methylation reactor 119 may have one or more methylation reactors (not shown) where the methylation catalyst and auxiliary catalyst are present. The product of the methylation conditions in the methylation reactor (the methylation product mixture effluent) can be a mixture of xylenes, water, methanol, dimethyl ether, and by-products and is fed from methylation reactor 119 through outlet 121 to line 123 and ultimately to heat exchanger 109 to be cooled. The cooled methylation product mixture effluent is passed through line 125 to heat exchanger 127 to be either heated or cooled as necessary to arrive at the desired temperature for separation, then through line 129 to separation subsystem 131. Separation subsystem 131 may contain one or more separation units (not shown). Separation subsystem 131 may separate methane or other light gases which can be removed via line 133 may be used as fuel gas (not shown).

Separation subsystem 131 may further separate a dimethyl ether-rich stream which is then provided to line 135, which can be recycled into methylating agent feed 101 or methylation reactor inlet 117. Line 135 may include pumps or compressors so that the DME-rich stream may enter the methylation agent feed or methylation reactor at a desired pressure, the combination of lines and pumps or compressors is a first recycling channel. The first recycling channel, may contain other combinations of lines and pumps or compressors (not shown) suitable to recycle DME to methylation reactor 119.

Separation subsystem 131 may further separate toluene-rich stream 137, which may contain benzene and can be recycled into aromatic hydrocarbon feed 103 or methylation reactor inlet 117. Line 137 may include pumps or compressors so that the toluene-rich stream may enter the aromatic hydrocarbon feed or methylation reactor at a desired pressure; the combination of lines and pumps or compressors is a second recycling channel. Furthermore, the separation may yield a xylenes-rich stream which is sent out of line 139, and line 139 may be connected to other systems for further processing (not shown). The xylenes-rich stream can be fed to a separation system such as a crystallizer or a simulated moving bed adsorption chromatography to recover a high-purity p-xylene product and produce a p-xylene-depleted stream. The p-xylene-depleted stream can be isomerized in an isomerization reactor in the presence of an isomerization catalyst to produce additional p-xylene.

Separation subsystem 131 may further separate a methanol-rich stream which is then provided to line 141, which can be recycled into methylating agent feed 101 or methylation reactor inlet 117. Line 141 may include pumps or compressors so that the methanol-rich stream may enter the methylation agent feed or methylation reactor at a desired pressure; the combination of lines and pumps or compressors is a third recycling channel. The third recycling channel, may contain other combinations of lines and pumps or compressors (not shown) suitable to recycle methanol to methylation reactor 119. Furthermore, the separation may yield a water-rich stream which is sent out of line 143, and line 143 may be connected to other systems for further processing (not shown), including wastewater purification systems (not shown).

EXAMPLES

Part A: Preparation of Methylation Catalysts

Example A1 (Comparative): Preparation of a MCM-49 Molecular Sieve Catalyst

MCM-49 crystals were fabricated pursuant to the teaching in U.S. Pat. No. 5,236,575. A MCM-49 molecular sieve catalyst comprising an alumina binder was made from a mixture of MCM-49 crystals (before calcination) and high surface area (having a specific area ≥250 m$^2$/g) alumina (80:20 weight ratio) that was combined in a mulling operation. A mixture of MCM-49, high surface area alumina, and water was extruded into 1/20" Quadra-lobes and then dried in oven at 121° C. overnight. The dried extrudate was calcined in nitrogen ($N_2$) at 538° C. to decompose and remove the organic template, used in the synthesis of MCM-49 crystals. The thus calcined extrudate was then humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. overnight and then calcined in air at 538° C. to obtain an H-form MCM-49 molecular sieve catalyst composition. The H-formed extrudate was measured to have a total surface area of 536 m$^2$/g, which includes a mesopore area of 184 m2/g, and a collidine adsorption of −71 μmoles/g. The alumina supported MCM-49 molecular sieve catalyst composition was grinded to smaller particles and then sieved. Particles with 60/100 mesh sizes were used in the reactor runs as a comparative methylation catalyst system without an auxiliary catalyst, and was used to make the inventive methylation catalyst system of Example A2 below.

Example A2 (Inventive): Preparation of a Methylation Catalyst System Comprising the MCM-49 Molecular Sieve Catalyst of Example A1 and Yttria Auxiliary Catalyst Yttria used as the auxiliary catalyst was purchased from Sigma Aldrich. The yttria from the vendor was shaped into 60/100 mesh particles by pelletizing, grinding, and sieving.

The shaped yttria auxiliary catalyst was physically well mixed with the 60/100 mesh H-form MCM-49 molecular sieve catalyst, with a weight ratio of the auxiliary catalyst to the MCM-49 molecular sieve catalyst of 1:3, to obtain a methylation catalyst system of this disclosure.

Part B: Toluene Methylation with Methanol Processes

The comparative MCM-49 molecular sieve catalyst prepared in Example A1 and the inventive methylation catalyst system were then tested for their performances in a toluene methylation with methanol process.

A sample of the comparative MCM-49 molecular sieve catalyst prepared in Example A1 or the inventive methylation catalyst system prepared in Example A2 was then loaded into a down flow fixed-bed steel reactor. A feed consisting of toluene and methanol at a toluene/methanol molar ratio of 3:1 was fed into the reactor. Pressure was controlled at 600 psig (4136 kPa, gauge pressure). Reactor temperature was controlled at 350° C. Weight hourly space velocity (WHSV) was controlled at 6.21 $hr^{-1}$. WHSV is defined as the ratio of the flow rate of the toluene/methanol feed to the weight of the alumina supported MCM-49 molecular sieve catalyst in both experiments.

The composition of the methylation product mixture effluent was analyzed by a gas chromatograph, equipped with a flame ionization detector. Toluene conversion and para-xylene selectivity were calculated from the gas chromatography analysis. Toluene conversion is defined as the change in toluene concentration between the feed and product, normalized by the toluene concentration in the feed. Para-xylene selectivity is defined as the para-xylene concentration in the $C_8$ fraction of the methylation product mixture effluent. All calculations were made on molar basis.

Example B1 (Inventive): Toluene Methylation with Methanol Using the Methylation Catalyst System Prepared in Example A2

In this exemplary methylation process, the inventive methylation catalyst system prepared in Example A2 was tested in a process as described above in this Part B.

Example B2 (Comparative): Toluene Methylation with Methanol Using the MCM-49 Molecular Sieve Catalyst Prepared in Example A1

In this exemplary methylation process, the comparative MCM-49 molecular sieve catalyst prepared in Example A1 was tested in a process as described above in this Part B.

Figure 2:
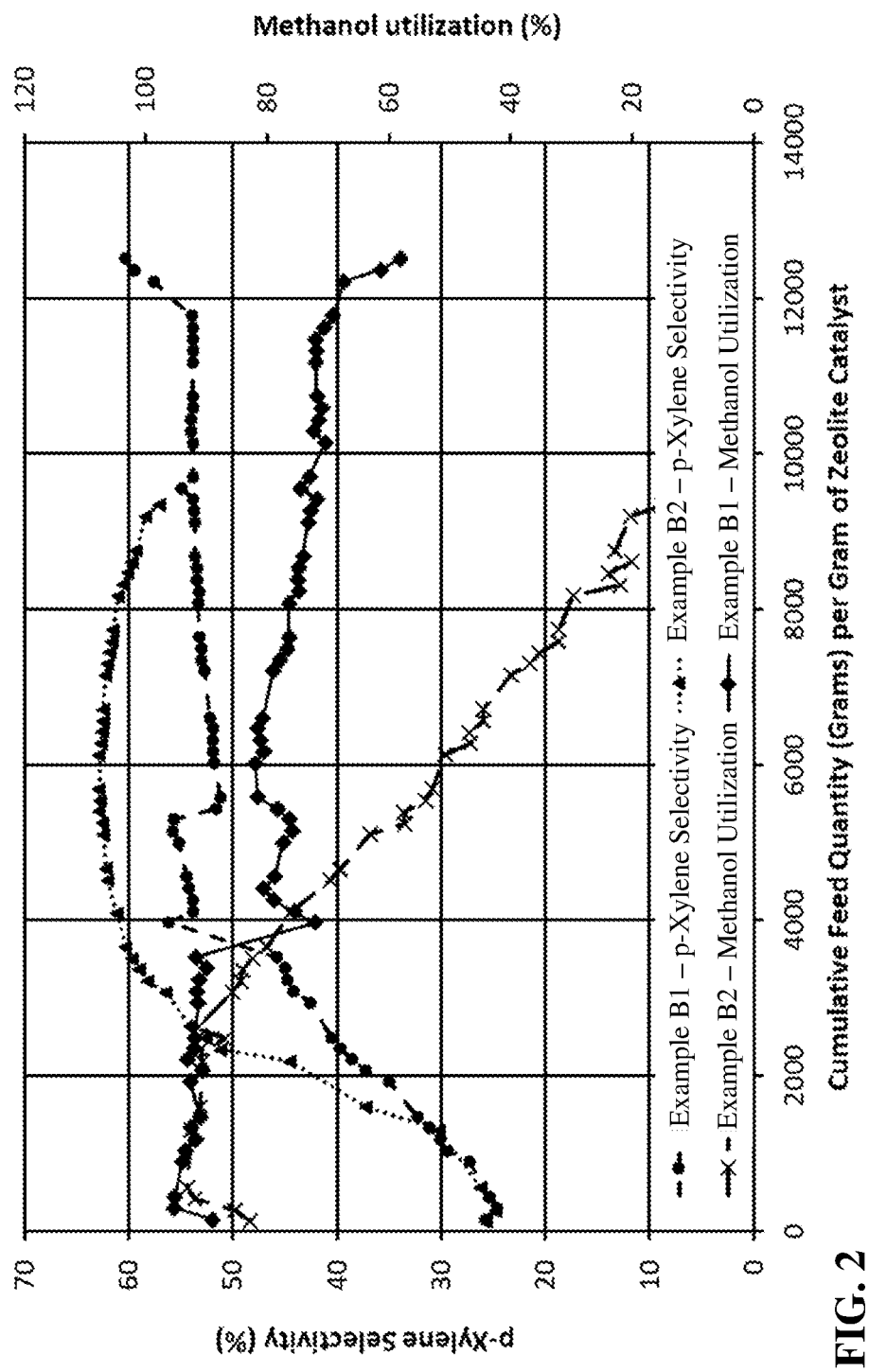
FIG. 2 is a graph showing methanol utilization and p-xylene selectivity as a function of cumulative quantity of total feed (grams) per gram of the molecular sieve catalyst in exemplary processes of this disclosure for converting toluene via methylation with methanol.

FIG. 2 illustrates catalyst performances over time. In FIG. 2, p-Xylene selectivity and methanol utilization are shown on the y-axes, and cumulative grams of feed per gram of catalyst are shown on the x-axis. FIG. 2 indicates that the process in comparative Example B2 using the comparative catalyst of comparative Example A1 had slightly higher p-xylene selectivity than the process in inventive Example B1 using the inventive methylation catalyst system of Example A2. However, in terms of methanol utilization, the process of the inventive Example B1 exhibits a curve with a slightly negative slope. In distinct contrast, the comparative process in Example B2 exhibits a curve with a steep negative slope. This demonstrates that the catalyst used in the process in comparative Example B2 had a much higher deactivation rate.

Figure 3:
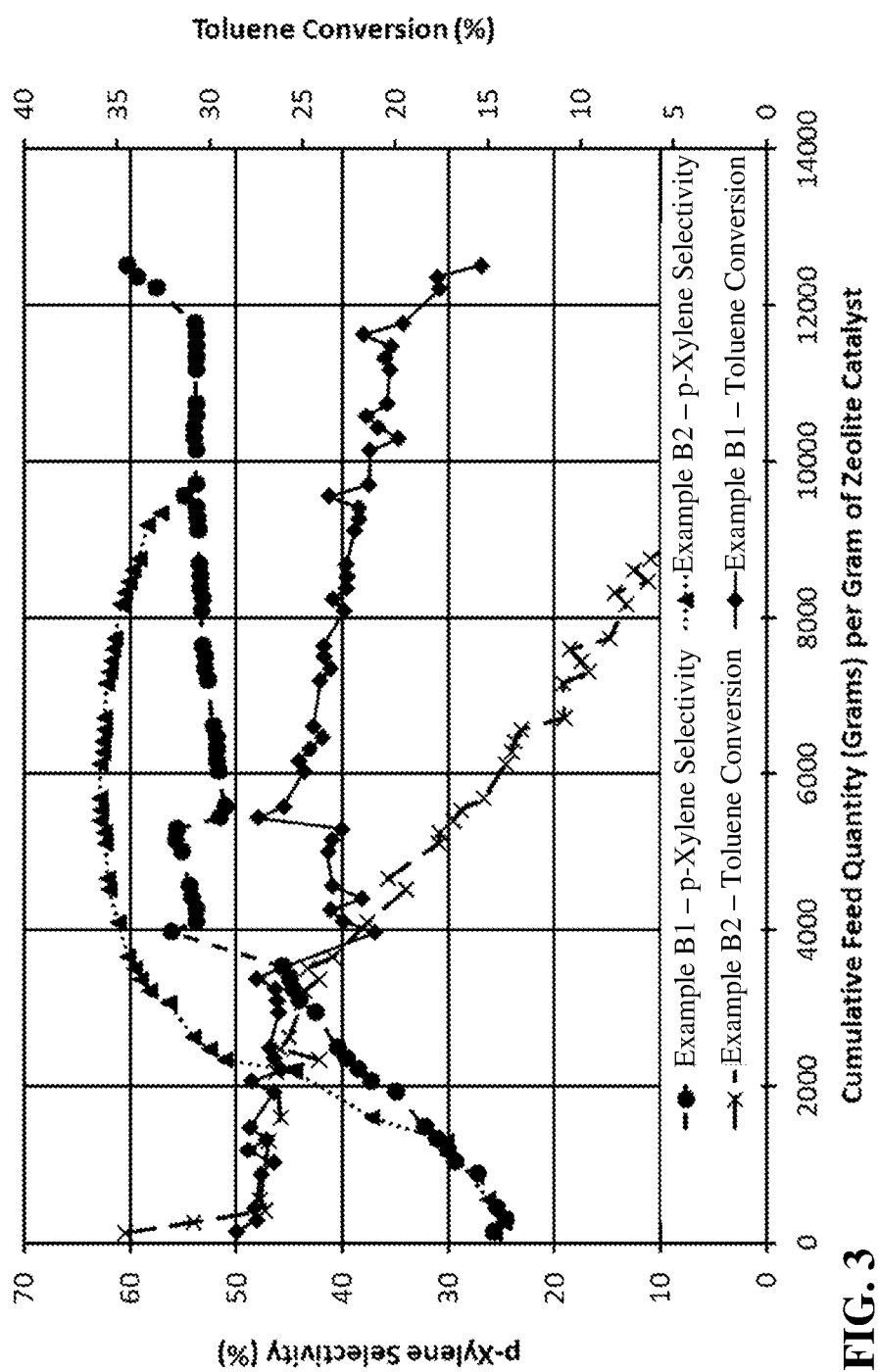
FIG. 3 is a graph showing toluene conversion and p-xylene selectivity as a function of cumulative quantity of total feed (grams) per gram of the molecular sieve catalyst in exemplary processes of this disclosure for converting toluene via methylation with methanol.

FIG. 3 illustrates catalyst performances over time. In this figure, p-xylene selectivity and toluene conversion are shown on the y-axes, and cumulative quantity (grams) of feed per gram of catalyst over time in a test run is shown on the x-axis. Cumulative quantity (grams of feed per gram of catalyst can be used to measure catalyst life. As can be seen from FIG. 3, p-xylene selectivity is 52% at 6000 cumulative grams of feed per gram of catalyst in the inventive process of Example B1 using the methylation catalyst system prepared in Example A2 comprising a 3:1 mixture of the MCM-49 molecular sieve catalyst and the yttria auxiliary catalyst. This is lower than the p-xylene selectivity of 63% in the comparative process of Example B2 using the comparative MCM-49 molecular sieve catalyst prepared in Example A1 without an auxiliary catalyst.

However, from FIG. 3, it is clear that in the inventive process of Example B1, toluene conversion was 25% at 6000 grams of cumulative feed per gram of catalyst. In contrast, in the comparative process of Example B2, toluene conversion was only 14% at 6000 grams of cumulative feed per gram of catalyst. The toluene conversion data clearly demonstrate that the deactivation rate is greatly decreased in Example B1, with the addition of the yttria auxiliary catalyst. Without being limited by theory, a possible explanation for the improved toluene conversion with yttria auxiliary catalyst is that some methanol had decomposed to formaldehyde and other coke precursors by the alumina supported MCM-49 catalyst or steel reactor wall, and these coke precursors were removed by yttria.

Overall, it has been found that inclusion of a metal-containing auxiliary catalyst in combination with a molecular sieve catalyst in a methylation catalyst system can suppress catalyst deactivation in processes for alkylation of benzene and/or toluene with methanol and/or dimethyl ether to produce p-xylene. Suppression of deactivation of methylation catalysts improves catalyst utilization between regeneration cycles, which decreases cost of production. Without addition of an auxiliary catalyst, more frequent catalyst regeneration processes may otherwise be required. The use of a methylation catalyst system including auxiliary catalysts can decrease the overall cost of p-xylene production by increasing the catalyst life cycle and decreasing the frequency of catalyst regenerations, which would also reduce the frequency of reactor shut-downs which otherwise interrupt p-xylene production.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A process for converting benzene and/or toluene, the process comprising:
   (a) feeding an aromatic hydrocarbon feed and a methylating agent feed into a methylation reactor, wherein the aromatic hydrocarbon feed comprises benzene and/or toluene, and the methylating agent comprises methanol and/or dimethyl ether; and
   (b) contacting the aromatic hydrocarbon feed with the methylating agent feed in the presence of a methylation catalyst system in the methylation reactor under methylation conditions effective to produce a methylation product mixture effluent, wherein the methylation catalyst system comprises a molecular sieve catalyst and an auxiliary catalyst, the molecular sieve catalyst comprises a molecular sieve of the MWW framework type, the auxiliary catalyst comprises a metal element selected from Group 2, Group 3, the lanthanide series, the actinide series, and mixtures and combinations thereof, and the methylation product mixture effluent comprises p-xylene, the methylation reaction conditions comprise an aromatic inlet feed temperature in a range from 200 to 500° C., an absolute pressure in a range from 100 to 8,500 kPa, a WHSV in a range from 5.0 hour$^{-1}$ to 15 hour$^{-1}$.

2. The process of claim 1, wherein the metal element is selected from yttrium and the lanthanide series of elements, and mixtures and combinations of two or more thereof.

3. The process of claim 1, wherein the metal element is yttrium.

4. The process of claim 1, wherein the auxiliary catalyst comprises an oxide of the metal element.

5. The process of claim 1, wherein the methylation catalyst system comprises a physical mixture of particles of the molecular sieve catalyst, particles of the auxiliary catalyst, and optionally particles of an inert component.

6. The process of claim 1, wherein the auxiliary catalyst is at least partly supported on the molecular sieve.

7. The process of claim 1, wherein the quantity of the auxiliary catalyst, expressed as weight percentage of the auxiliary catalyst based on the total weight of the molecular sieve catalyst and the auxiliary catalyst, is in a range from 1 to 50 wt %.

8. The process of claim 1, wherein the quantity of the auxiliary catalyst, expressed as weight percentage of the auxiliary catalyst based on the total weight of the molecular sieve catalyst and the auxiliary catalyst, is in a range from 5 to 30 wt %.

9. The process of claim 1, wherein in (a), the methylation catalyst system is present in the methylation reactor in a fixed bed.

10. The process of claim 1, wherein in (b), the methylation reaction conditions comprise a temperature in a range from 250 to 450° C.

11. The process of claim 1, wherein the molar ratio of the aromatic hydrocarbon feed to the methylating agent feed is R(a/m), wherein $$R(a/m) = \frac{M(tol) + 2 \cdot M(bz)}{M(\text{methanol}) + 2 \cdot M(DME)},$$

where M(tol) and M(bz) are the moles of toluene and benzene in the aromatic hydrocarbon feed, respectively, and M(methanol) and M(DMF) are the moles of methanol and dimethyl ether in the methylating agent feed, respectively, and wherein 1≤R(a/m)≤5.

12. The process of claim 11, wherein 2≤R(a/m)≤4.

13. The process of claim 1, wherein in (b), the methylation reaction conditions comprise a weight hourly space velocity in a range from 5 hour$^{-1}$ to 10 hour$^{-1}$ based on the flow rate of the aromatic hydrocarbon feed and the methylating agent feed and the weight of the molecular sieve catalyst.

14. The process of claim 1, wherein the methylation product mixture effluent further comprises methanol and dimethyl ether, and the process further comprises:
   (c) obtaining a dimethyl ether-rich stream from at least a portion of the methylation product mixture effluent; and
   (d) recycling at least a portion of the dimethyl ether-rich stream obtained in (c) to (a) as at least a portion of the methylating agent feed.

15. The process of claim 14, wherein all of the dimethyl ether contained in the methylating agent feed in (a), if any, is the dimethyl ether recycled in (d) to (a), based on the total weight of the dimethyl ether in the methylating agent feed.

16. The process of claim 14, wherein (c) comprises:
   (c1) separating the methylation product mixture effluent to obtain an aqueous phase and an oil phase; and
   (c2) separating the oil phase to obtain the dimethyl ether-rich stream of (c) and an aromatics-rich stream.

17. The process of claim 16, wherein (c) further comprises:
   (c3) separating the aromatics-rich stream to obtain a toluene-rich stream and a xylenes-rich stream; and
   (c4) recycling at least a portion of the toluene-rich stream obtained in (e) to (a) as at least a portion of the aromatic hydrocarbon feed.

18. The process of claim 16, wherein (c) further comprises:
   (c5) distilling the aqueous phase obtained in (el) to obtain a methanol-rich stream and a water-rich stream; and
   (c6) recycling at least a portion of the methanol-rich stream obtained in (c5) to (a) as at least a portion of the methylating agent feed.

19. The process of claim 1, wherein the aromatic hydrocarbon feed comprises at least 90 wt % of toluene, based on the total weight of the aromatic hydrocarbon feed.

20. The process of claim 1, wherein the molecular sieve is selected from MCM-22, PSH-3, SSZ-25, ERB-1, ITQ-1, MCM-36, MCM-49, MCM-56, EMM-10, EMM-12, EMM-13, UZM-8, UZM-8HS, UZM-37, UCB-3, and mixtures of two or more thereof.

21. The process of claim 20, wherein the molecular sieve is selected from MCM-22, MCM-49, and mixtures thereof.

22. A process for converting benzene and/or toluene to xylenes, the process comprising:
- (a) feeding an aromatic hydrocarbon feed and a methylating agent feed into a methylation reactor, wherein the aromatic hydrocarbon feed comprises benzene and/or toluene, and the methylating agent comprises methanol and/or dimethyl ether; and
- (b) contacting the aromatic hydrocarbon feed with the methylating agent in the presence of a methylation catalyst system under methylation reaction conditions effective to produce a methylation product mixture effluent, wherein the methylation catalyst system comprises a molecular sieve catalyst and an auxiliary catalyst, the molecular sieve catalyst comprises a MWW framework type zeolite, the auxiliary catalyst comprises an oxide of a metal element selected from Group 2, Group 3, the lanthanide series, the actinide series, and mixtures and combinations thereof, and the methylation product mixture effluent comprises p-xylene, the methylation reaction conditions comprise an aromatic inlet feed temperature in a range from 200 to 500° C., an absolute pressure in a range from 100 to 8,500 kPa, a WHSV in a range from 5.0 to 10, and a molar ratio of the aromatic hydrocarbon feed to the methylating agent feed of R(a/m), where $$R(a/m) = \frac{M(tol) + 2 \cdot M(bz)}{M(\text{methanol}) + 2 \cdot M(DME)},$$

M(tol) and M(bz) are the moles of toluene and benzene in the aromatic hydrocarbon feed, respectively, and M(methanol) and M(DME) are the moles of methanol and dimethyl ether in the methylating agent feed, respectively, and $1 \leq R(a/m) \leq 5$.

* * * * *